United States Patent [19]

Howe

[11] Patent Number: 4,819,625

[45] Date of Patent: Apr. 11, 1989

[54] NEBULIZER HEATER

[75] Inventor: Blair E. Howe, Rancho Santa Margarita, Calif.

[73] Assignee: Cimco, Inc., Costa Mesa, Calif.

[21] Appl. No.: 120,080

[22] Filed: Nov. 12, 1987

[51] Int. Cl.[4] .............................................. A61M 11/00
[52] U.S. Cl. ........................ 128/200.18; 128/200.14; 128/200.21; 261/DIG. 65
[58] Field of Search ...................... 128/200.18, 203.17, 128/203.27, 203.16, 203.26, 204.17, 200.21, 200.14; 261/DIG. 65, 142; 219/271, 273, 275, 276, 302, 303, 304

[56] References Cited

U.S. PATENT DOCUMENTS

| | | | |
|---|---|---|---|
| 1,323,181 | 11/1919 | Goodfellow | 128/203.27 |
| 2,226,582 | 12/1940 | Robinson | 128/192 |
| 2,366,753 | 1/1945 | Robinson | 219/38 |
| 3,659,604 | 5/1972 | Melville et al. | 128/212 |
| 4,036,919 | 7/1977 | Komendowski et al. | 261/DIG. 65 |
| 4,100,235 | 7/1978 | Thornwald | 219/271 |
| 4,101,611 | 7/1978 | Williams | 261/142 |
| 4,134,940 | 1/1979 | Sherman | 261/DIG. 65 |
| 4,190,046 | 2/1980 | Virag | 128/200 |
| 4,201,737 | 5/1980 | Carden | 261/DIG. 65 |
| 4,427,004 | 1/1984 | Miller | 128/200 |
| 4,460,819 | 7/1984 | Eugster | 219/302 |
| 4,546,697 | 10/1985 | Schaeffer | 219/275 |
| 4,629,590 | 12/1986 | Bagwell | 261/DIG. 65 |

Primary Examiner—Edgar S. Burr
Assistant Examiner—Aaron J. Lewis
Attorney, Agent, or Firm—Gausewitz, Carr & Rothenberg

[57] ABSTRACT

A nebulizer providing a moistened breathing mixture of aerosol for inhalation therapy is provided with an improved heater having a single heating element arranged in a heating housing, configured so as to support and heat the liquid in the nebulizer container and to also heat the aerosol discharged from the nebulizer so as to most efficiently utilize the heat energy and to most efficiently transfer heat energy from the heater to the aerosol. Passage of the aerosol through and accumulation in the relatively long annular accumulator that circumscribes the heater collects rain out from the aerosol and re-vaporizes the collected liquid to add further moisture to the aerosol.

17 Claims, 1 Drawing Sheet

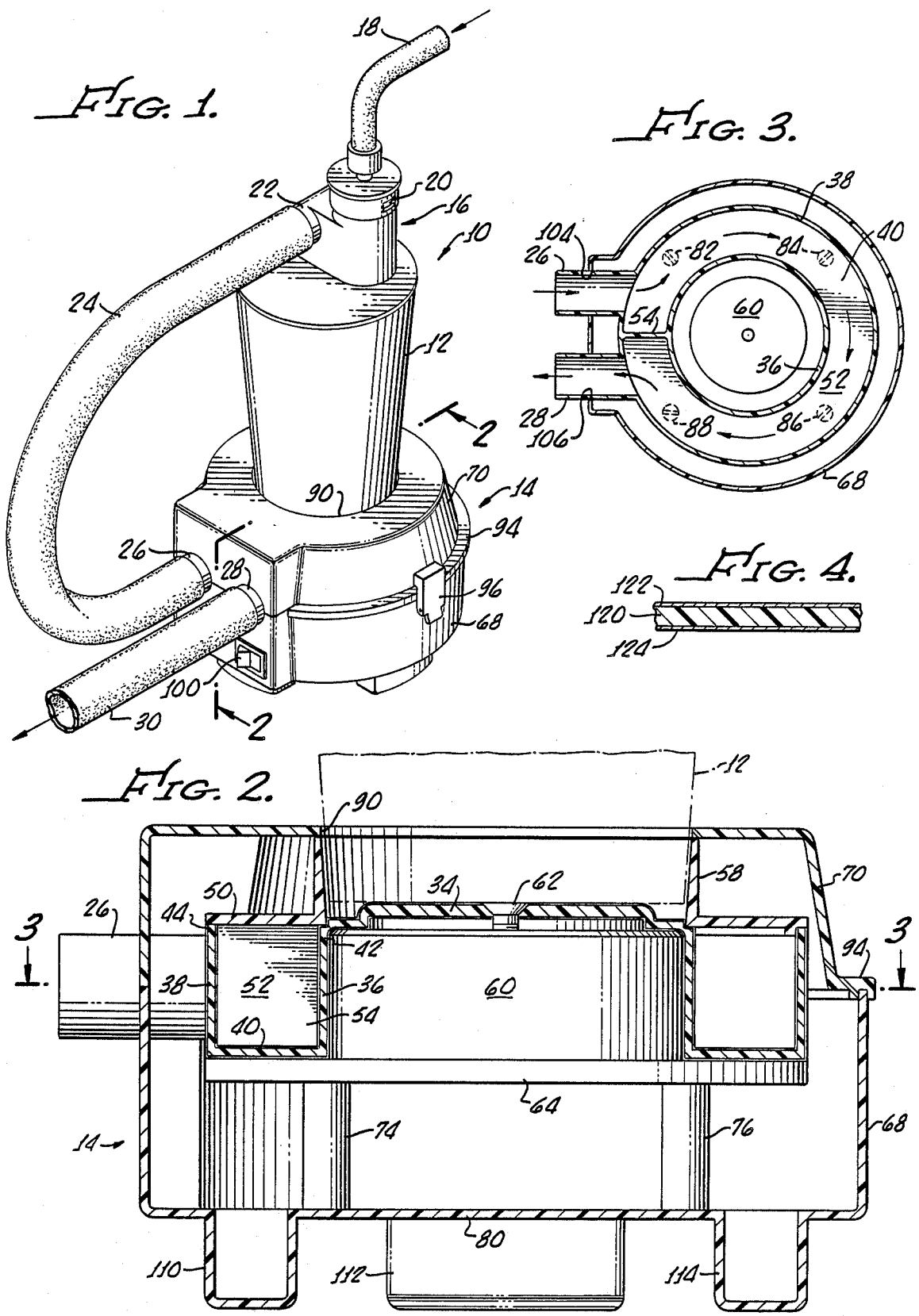

NEBULIZER HEATER

BACKGROUND OF THE INVENTION

The present invention relates to nebulizers for inhalation therapy, and more particularly concerns a nebulizer having an improved arrangement for heating both the container liquid and the aerosol produced by the nebulizer.

Nebulizers are commonly used for inhalation therapy to provide moist warm oxygen enriched breathing mixture to the patient. In many types of nebulizer a stream of oxygen is passed through a restrictive nozzle to increase its velocity and provide a venturi effect that sucks liquid from a container connected with a mixing chamber. The high speed stream of oxygen is mixed with ambient pressurized air and entrains water that is drawn up from the container by the low pressure of the venturi effect of the oxygen stream of high velocity.

The aerosol breathing mixture reaching the patient must have a temperature not less than ambient room temperature and moreover should have a significant content of water vapor. Various factors tend to lower the aerosol temperature including the relatively long path of aerosol flow through the tubing from the nebulizer to the patient and, in particular, the operation of the air water and oxygen mixing chamber, which often involves a decreased pressure due to at least the venturi action of the high speed jet. In the mixing chamber, expansion of the compressed oxygen will lower its pressure and thus effectively decrease the temperature of the resulting aerosol.

Many attempts have been made to heat either the aerosol or the container liquid but these have not been successful. Nebulizer heaters presently available are considered to be unsatisfactory. It is difficult to heat the aerosol directly, because the mixture, which is basically a gas, has low heat transmissivity, and thus efficiency of prior aerosol heaters has been low. Attempts to heat the aerosol by heating the water in the container before it is mixed with the air oxygen mixture also have been unsatisfactory in that it is difficult to transfer sufficient amounts of heat to the aerosol by means of heating the water. Moreover, having raised the temperature of the resulting aerosol by heating the water, the aerosol becomes more susceptible to "rain out", which means that water vapor in the aerosol tends to condense into larger droplets and to fall from the aerosol into the connecting tubing. The problem of water collecting in the connecting tubing between the nebulizer and the patient is significant, not only because of the fact that the aerosol reaching the patient has less moisture, but because water collecting in the tubing could block the tubing and prevent flow of any inhalation mixture to the patient.

Accordingly it is an object of the present invention to provide an aerosol heater that avoids or minimizes above mentioned problems.

SUMMARY OF THE INVENTION

In carrying out principles of the present invention in accordance with a preferred embodiment thereof, a nebulizer heater is provided having a heat transfer housing that forms a heater mounting chamber having a heater therein, an accumulator and aerosol passage adjacent the chamber, and a container support adjacent the chamber. The liquid container is heated from the heater mounting chamber and aerosol from the nebulizer flows through the aerosol accumulator adjacent the heater chamber before being passed on to the patient. In a particular embodiment the aerosol accumulator completely circumscribes the heater chamber, providing a relatively long large diameter passage, and thus a relatively long dwell time for transfer of heat from the heater chamber to the aerosol in the accumulator. The same heated aerosol accumulator collects rain out or water droplets precipitating from the aerosol, heats the water falling from the aerosol and evaporates it for recapture by the flowing stream of aerosol. Thus the heater of the present disclosure provides a number of functions. It provides a support for the entire nebulizer, with the container sitting directly atop the heater chamber. It heats the container liquid. It heats the aerosol over a relatively long flow path and, still further, it collects and re-vaporizes water dropping out of the aerosol.

BRIEF DESCRIPTION OF THE DRAWINGS

FIG. 1 is a pictorial view of a nebulizer and heater embodying principles of the present invention;

FIG. 2 is a section taken on lines 2—2 of FIG. 1;

FIG. 3 is a section taken on lines 3—3 of FIG. 2; and

FIG. 4 is a fragmentary sectional view showing details of the coated plastic that forms structual elements of the heater housing.

DETAILED DESCRIPTION

As illustrated in FIG. 1 a nebulizer, generally indicated at 10, includes a container 12 having its lower portion resting upon and generally confined in a base type heater, generally indicated at 14. The nebulizer may be of the type shown in U.S. Pat. No. 4,629,590 to Bagwell, which describes a nebulizer sold by Cimco, assignee of the present application. The nebulizer container 12 confines a body of sterile water and includes an upper portion having secured thereto a mixer 16, which receives oxygen under pressure from an oxygen input conduit 18. By means of a mixing jet (not shown) contained within the mixer 16, liquid is drawn from the bottom of the container 12 for mixing in a mixing chamber with the pressurized oxygen and with ambient air drawn into the mixing chamber through an aperture 20 in the mixer. Thus, the mixer of the nebulizer provides a output stream, via an output fitting 22, of a moisturized mixture of air and oxygen for use in inhalation therapy. Further details of this nebulizer are shown in U.S. Pat. No. 4,629,590.

According to the present invention a heater assembly 14 is provided to perform a number of different functions. First, the heater assembly provides a support and a base upon which the nebulizer rests. Second, the heater assembly provides direct heat transfer to the bottom and sides of the bottom of the container 12, to directly heat water within the container. Third, the heater assembly provides an elongated aerosol accumulator of high volume and large cross sectional area for heating the aerosol provided by the nebulizer. This aerosol accumulator receives aerosol produced by the nebulizer via a connecting conduit 24, having one end connected to the nebulizer output fitting 22 and the other end connected to an input fitting 26 on the heater assembly. The aerosol accumulator within the heater assembly terminates in an output fitting 28, to which is connected an output conduit 30 that is connected to a patient breathing apparatus (not shown).

A fourth function of the described heater assembly is its collection of rain out from the aerosol of the nebulizer as it flows through and is temporarily stored in the aerosol passage. The heater assembly heats precipitated water droplets to revaporize the water so that it will be again entrained within the nebulizer aerosol.

The heater assembly comprises a heat transfer housing, illustrated in cross section in FIG. 2, having a circular top support plate 34 and a depending continuous peripheral wall 36 fixed to the outer edges of the plate 34. A second continuous peripheral wall 38, spaced from the inner wall 36 and running parallel thereto, completely encircles the inner wall 36 and is fixedly connected to the bottom of the inner wall 36 by a continuous annular bottom wall 40, fixedly secured to the bottoms of both the inner and outer walls 36 and 38. Walls 36, 38 and 40 preferably are integral with top plate 34. Fixedly connected to and extending across upper edges 42, 44 of inner and outer walls 36 and 38 is a continuous annular top wall 50, which cooperates with the sidewalls 36, 38 and bottom wall 40 to provide a sealed completely closed continuous annular aerosol passage and accumulator 52.

As best seen in FIG. 3 tubular input and output fittings 26, 28 are integrally formed with the circular outer wall 38 and a single baffle or partition 54 extends across the aerosol passage, from the inner wall 36 to the outer wall 38, so as to provide a continuous flow passage and temporary storage chamber. Aerosol will flow in through fitting 26, thence in a clockwise direction, as indicated by the arrows, around the aerosol accumulator passage 52, and thence outwardly through output fitting 28. Aerosol remains in the accumulator 52 because of its relatively large volume and because its cross sectional area is made larger than that of the input and output ports and conduits.

A relatively short rigid upstanding container support wall 58 is fixed to the outer edge of top plate 34 and to the upper edge of inner wall 36 and extends continuously around the bottom of container 12 to confine the bottom of the container within a heater recess formed by support wall 58 and top plate 34. Top plate 34 and inner wall 36 cooperatively define a downwardly facing heater mounting chamber of generally circular cylindrical form which snugly mounts a circular cylindrical and heat conductive heater housing 60 containing suitable heater elements (not shown). Heater housing 60 may be secured within the heater chamber and to the top plate 34 by means of fastener means such as for example a screw 62. Heater housing 60 includes a heater housing bottom plate 64 of circular configuration and extending along and in heat conductive contact with the full extent of bottom wall 40, to provide maximum heat flow from the heater to the bottom plate.

The heat transfer housing and the heater housing 60 are mounted in a heater assembly housing formed of an inter-fitting base 68 and a heater assembly housing top 70. Housing base 68, formed of a suitable rigid plastic, is of a circular configuration, having four mutually spaced and fixed internal supporting posts 74, 76, and others (not shown) projecting upwardly from a bottom 80 of the base 68. Each post has a vertically extending threaded aperture for receiving respective ones of a plurality of screws 82, 84, 86 and 88, (FIG. 3) which extend through the heater housing bottom plate 64 into the apertures in supporting posts 74, 76 etc. The assembly housing top part 70 has a central aperture 90, through which the bottom of the container 12 extends for support by the heater top support plate 34. Inner edges of the apertured top of assembly housing top 70 rest on upper edges of container support wall 58. A peripheral flange 94, outwardly extending from the assembly housing top, cooperates with a pair of oppositely positioned pivoted latches 96 (only one of which is shown) mounted on the assembly housing base 68 to detachably secure the two parts of the assembly housing to one another. A manually operable switch 100, (FIG. 1) mounted on the assembly housing base 68 is provided to control the heater elements which are connected to a suitable source of electrical power by means of an electrical lead and temperature regulating circuitry or the like (not shown), that may be mounted within assembly housing base 68 below the heater housing bottom plate 64. The top and bottom parts of the assembly housing are provided with mating semicircular recesses to form circular apertures (FIG. 3) 104, 106 through which the fittings 26 and 28 extend.

The entire heater assembly is supported on four legs, of which three, indicated at 110, 112, and 114 are shown, which are formed integrally with and depend from the bottom 80 of the bottom part of the heater assembly base 68.

Heater housing 60 and its bottom plate 64 are made of a suitable metal having high heat conductivity such as for example aluminum, whereas the heat transfer housing is made of a light weight plastic having improved heat transfer and cleaning characteristics provided by a heavy metal coating. Thus, as illustrated in FIG. 4, the heat transfer housing including top support plate 34, walls 36, 38, and 40, (but not walls 50 and 58) are formed of a plastic material 120 coated on both sides with heavy, thick coatings 122, 124 of suitable metal. Presently preferred for such coatings are combinations of electroless copper, electroless nickel and chromium, formed in layers, one upon the other and deposited upon both sides of the interposed plastic 120. By this means the plastic is provided with good heat transfer characteristics and a smooth easily cleaned surface, and the parts are still readily manufactured of inexpensive and readily formed plastic. The entire heat transfer housing is readily removable for sterilization. Walls 50, 58 are made of the same plastic as the other walls, but need not be coated with metal.

In operation of the device, oxygen under pressure is fed to the mixer 16 via oxygen input conduit 18 and mixed with fine water droplets or vapor derived from water contained in the container 12 to provide an aerosol discharge via fitting 22 and connecting the conduit 24. The aerosol flows from the conduit 24 through heater assembly input fitting 26 and thence in a substantially 360 degree path through the aerosol accumulator and passage 52 which closely encircles the heater chamber that contains the heater housing 60. Aerosol remains in the accumulator for a relatively increased time. Aerosol then flows through the output port 28 to connecting tubing 30. The container 12, which is resting upon heat transfer housing plate 34 and confined within the circular container support wall 58, has its contents heated by transfer of heat from the heater through the plate 34. Temperature of the aerosol is raised by using water heated in the container by the heater and also by temporarily retaining the aerosol in the accumulator adjacent the very same heater that heats the container. The flow of aerosol through and time of storage within the passage or accumulator 52 is of sufficiently long duration to enable liquid collecting in the bottom of the passage, due to rain out from the aerosol, to be heated, vaporized and recombined with the flowing aerosol. Thus the described heater is effective not only to heat the aerosol provided from the apparatus but also significantly improves its moisture content.

The entire apparatus is readily disassembled for cleaning and sterilization. To disassemble the apparatus, latches 96 are disengaged and the hoses are disconnected. Container 12 is removed from the heater assembly and the the assembly housing top 70 is removed from the base 68. The heat transfer housing, comprising the walls 36, 38, top support plate 34, bottom plate 40, and walls 50 and 58 are readily removed as an integral unit from the heater housing 60 which remains fixably secured to the assembly housing base 68 by means of the screws 82 through 88. The heat transfer housing may then be readily cleaned and sterilized. The chromium plated surfaces of the aerosol passage and of the heat transfer housing top plate 34 are smooth and readily cleaned and sterilized.

The described heater assembly is easily adapted for use with nebulizers of different types and different configurations. It is only necessary to change the configuration of the container receiving recess defined by the top support plate 34 and support wall 58, and also the size of opening 90, to enable the heater to receive, support and operate upon a nebulizer having a container of different size, shape or configuration.

The assembly housing provides protection for the heating unit and the heat transfer housing. It prevents heat loss and also protects the controls and electric elements from accidental spillage of water. The housing serves as an insulator and also prevents accidental contact with electrical elements within the assembly housing base.

As mentioned above, a significant aspect of the described construction and configuration of the heater is the fact that the aerosol accumulator or passage not only has a relatively large volume but also has a large cross sectional area. In a presently preferred embodiment the cross sectional area of the annular aerosol passage 52 is approximately twice the cross sectional area of either of the conduits 24 or 30, which are of a size normally employed in devices of this kind. The increased volume and area of the aerosol passage provides a number of advantages. The large volume causes the annular passage to act as an accumulator or reservoir so that aerosol produced by and discharged from the mixer 16 is effectively stored in the passage 52 for a period of time before it is discharged through the relatively small cross sectional area output port 28. Thus, because the formed aerosol is stored for a short period of time within the accumulator or chamber 52, there is more time for large water droplets to be precipitated from the aerosol and, importantly, there is more time for the accumulated water already precipitated in the accumulator chamber to be vaporized and re-introduced into the aerosol within the accumulator chamber. Another advantage of the relatively large cross sectional area of the accumulator 52 is the fact that it has a larger surface area to provide a much greater area of contact between its heated wall and the aerosol that is temporarily stored therein.

There has been described an improved nebulizer heater assembly which employs but a single heating unit to heat both the liquid in the nebulizer container and the aerosol produced by the nebulizer, while at the same time collecting rain out from the produced aerosol and reintroducing the collected rain out as water vapor into the aerosol.

I claim:

1. In a nebulizer having a liquid container confining a body of liquid, mixing means secured to the container for receiving a compressed gas, for drawing liquid from the container, and for mixing the liquid and gas to provide an aerosol stream having droplets of said liquid entrained in said gas, improved heating apparatus for heating both the aerosol stream and the liquid confined in the container comprising:
   a heat transfer housing including,
      a heater mounting chamber,
      a heater in said chamber,
      an aerosol accumulator chamber adjacent said heater mounting chamber and in heat conductive relation thereto, and
      a container support adjacent said heater mounting chamber and in heat conductive relation thereto,
         said container support being adapted to support said liquid container in heat conductive relation thereto,
   means for flowing aerosol from said mixing means into and from said aerosol accumulator chamber, and output means for providing a heated aerosol stream from said housing, whereby said heater will heat both liquid confined in said container and aerosol accumulated in said accumulator chamber.

2. The apparatus of claim 1 wherein said accumulator chamber includes means for receiving and collecting liquid precipitated from the aerosol during flow of the aerosol through the accumulator chamber, whereby liquid collected in said accumulator chamber is heated by said heater and vaporized for mixing with said aerosol.

3. The heating apparatus of claim 1 wherein said container support includes a top support plate, said accumulator chamber having a peripheral wall portion depending from said top support plate and forming a heater receiving recess that is open at one end and closed at the other end, said recess defining said heater mounting chamber, said heater being mounted within said recess in contact with said peripheral wall portion, and means spaced from end extending along said wall portion for cooperating with said wall portion to define said accumulator chamber.

4. The heating apparatus of claim 3 including an upstanding peripheral support wall connected with and circumscribing said top support plate to define a container recess for receiving and retaining the bottom of said liquid container.

5. The heating apparatus of claim 1 wherein said accumulator chamber comprises an annular accumulator passage having input and output ports and substantially completely circumscribing said heater mounting chamber, said heater mounting chamber having an outer peripheral wall forming an inner wall of said annular accumulator passage.

6. The heating apparatus of claim 5 wherein said means for flowing aerosol from said stream and said output port comprises flow conduits having a cross sectional area not greater than a first value, and wherein said accumulator passage has a cross sectional area of more than about twice said first value, said accumulator chamber being configured to collect, to temporarily store and to re-vaporize rain out from said aerosol.

7. The heating apparatus of claim 5 wherein said heater includes a heater housing having a flat bottom plate extending along and in heat transmitting contact with a bottom wall of said container.

8. A nebulizer comprising:
a container adapted to confine a body of liquid therein,
a mixing chamber connected with the container for mixing liquid from said container with a gas and forming an aerosol,
a heater housing top support plate having one side contacting and supporting a bottom of said container,
a depending peripheral wall connected with said support plate and forming therewith a heater receiving chamber below the support plate,
means secured to the support plate for defining an annular aerosol accumulator circumscribing the depending wall, said aerosol accumulator having input and output ports,
conduit means for conducting aerosol from the mixing chamber nebulizer to said input port,
means connected to said output port for discharging heated aerosol, and
a heater in said chamber in heat transferring contact with the other side of said support plate and said depending wall.

9. The nebulizer of claim 8 including an upwardly extending peripheral container support wall fixed to and circumscribing said support plate, said last mentioned wall extending around and confining a lower portion of said container.

10. The nebulizer of claim 8 wherein at least some of said support plate, said conduit and said depending wall are formed of a rigid plastic material coated on both sides thereof with a thick layer of heat conductive metal.

11. The nebulizer of claim 9 wherein said heater includes the heater housing having a bottom plate extending outwardly from said peripheral depending wall and along and below said aerosol accumulator in heat transmitting relation thereto, a housing base having heater supporting means therein, said heater bottom plate resting upon said heater supporting means, and a housing cover connected to said housing base and circumscribing said aerosol accumulator and said container support wall to thereby enclose the heater, the bottom of the container, the container support wall and the aerosol accumulator.

12. A nebulizer and heater combination comprising:
a container having a body of liquid confined therein, said container having a lower portion and upper portion,
mixing means secured to said upper portion of the container for receiving a compressed gas and for mixing liquid from said container with said gas to provide an aerosol discharge,
heating means for supporting said container, for heating liquid within said container and for heating aerosol discharged from the nebulizer, said heating means comprising:
inner and outer mutually concentric and mutually radially spaced annular sidewalls each having top and bottom ends,
an annular accumulator bottom wall connecting bottom ends of said sidewalls to provide an annular recess closed at the bottom thereof,
a top support plate connected to and extending across the top ends of said inner annular sidewall and cooperating therewith to define a downwardly opening heater receiving recess,
an annular top wall connecting top ends of said inner and outer walls and sealing said annular recess to define an annular aerosol accumulator,
a partition extending across said annular accumulator,
input and output ports connected with said accumulator on opposite sides of said partition,
an upwardly extending container support wall secured to outer peripheral edges of said top support plate and defining therewith an upwardly opening container receiving recess, the bottom portion of said container being received within said last mentioned recess,
a heater assembly housing enclosing said heater, said heater recess, said aerosol accumulator and said container receiving recess, said heater assembly housing including means for supporting the heater and the nebulizer, and
conduit means for flowing discharged aerosol from said mixing means at the upper portion of said container to said input port, whereby liquid in said container is heated by contact between the top support plate and the bottom of said container, aerosol from the mixing chamber of the nebulizer is caused to flow through said annular aerosol accumulator adjacent said heater and is discharged with increased temperature from said output port, and water precipitated from the aerosol in said annular aerosol accumulator is heated and vaporized.

13. A nebulizer for producing a stream of moisturized gas for inhalation therapy, said nebulizer comprising:
a container having a circular wall for confining a quantity of liquid, having an upper portion and a lower portion,
said container including a mixing body connected to said upper portion of said container,
means in said mixing body for projecting a stream of gas toward the interior of the container,
means in the mixing body for drawing liquid from the container and mixing such liquid with the stream of gas to provide a stream of moisturized gas,
output port means for discharging moisturized gas from the container,
means for supporting said container and heating both the liquid in the container and the discharged moisturized gas, said last mentioned means comprising a heat transfer housing for receiving and supporting said lower portion of said container and for providing heat to said container and to said moisturied gas, and
conduit means for flowing moisturized gas discharged from the container into said heat transfer housing, said heat transfer housing comprising:
a top plate support in contact with and supporting said lower portion of said container,
an aerosol accumulator housing section defining an annular conduit circumscribing outer edges of said top support plate and extending downwardly therefrom, said aerosol accumulator housing section having an inner wall cooperating with said top plate to define a downwardly opening heater receiving recess,
a heater received in said recess and having an upper portion in heat transmitting contact with a lower side of said top support plate and having an outer side in contact with an inner wall of said aerosol accumulator housing section, a peripheral container support wall secured to an outer peripheral edge of said top support plate and extending upwardly therefrom along sides of said lower portion of said container, and a heater assembly housing surrounding and supporting said aerosol accumulator housing section, said heater recess and said container support top plate.

14. The nebulizer of claim 13 wherein said top plate, said aerosol accumulator housing section and said container supporting sidewall are formed of a plastic material having thick heat conductive metal coatings on both sides thereof.

15. The apparatus of claim 1 wherein said container support is adapted to removably confine a lower portion of the liquid container.

16. The apparatus of claim 1 wherein said container support is adapted to removably confine a lower portion of the liquid container and to transfer heat to the bottom and sides of the bottom of the liquid container.

17. A heated nebulizer comprising:
a liquid container,
a body of water in the container,
mixing means secured to an upper portion of the container for mixing oxygen with water from the container to generate a stream of aerosol formed of a mixture of oxygen and air having droplets of water entrained therein,
a heater comprising:
  a heater housing having a heater chamber and a container receiving recess separated by a container contact plate,
  a heater in said chamber,
  a lower portion of said container being positioned within the recess and being adjacent said contact plate,
  an accumulator chamber in contiguous heat conductive relation to and encircling at least part of said heater chamber, said accumulator chamber having input and output ports, and
conduit means for flowing said stream of aerosol to the input port of said accumulator chamber, whereby water is heated in the container before it is mixed with oxygen in the mixing means, and the stream of aerosol flows into and through said accumulator chamber between said input and output ports to absorb heat from the heater chamber, and wherein water droplets that may precipitate in said accumulator chamber from said stream of aerosol are heated and re-introduced into the aerosol as it flows through the accumulator chamber.

* * * * *